(12) United States Patent
Roff

(10) Patent No.: US 6,850,890 B1
(45) Date of Patent: Feb. 1, 2005

(54) SYSTEM AND METHOD FOR REINFORCING REGULAR CHIROPRACTIC TREATMENT

(76) Inventor: Roger R Roff, 200 E. Roosevelt St., Dillon, SC (US) 29536

( * ) Notice: Subject to any disclaimer, the term of this patent is extended or adjusted under 35 U.S.C. 154(b) by 710 days.

(21) Appl. No.: 09/132,285

(22) Filed: Aug. 11, 1998

Related U.S. Application Data

(60) Provisional application No. 60/055,239, filed on Aug. 12, 1997.

(51) Int. Cl.[7] .............................................. G06F 17/60
(52) U.S. Cl. ................................. 705/4; 705/2; 705/14
(58) Field of Search ................................ 705/2, 3, 4, 9, 705/14; 364/705.06, 705.08; 708/110, 112

(56) References Cited

U.S. PATENT DOCUMENTS

| | | | |
|---|---|---|---|
| 4,858,121 A | * | 8/1989 | Barber et al. ................... 705/2 |
| 4,987,538 A | | 1/1991 | Johnson et al. |
| 5,070,452 A | * | 12/1991 | Doyle, Jr. et al. ............... 705/2 |
| 5,182,705 A | | 1/1993 | Barr et al. |
| 5,225,976 A | | 7/1993 | Tawil |
| 5,301,105 A | * | 4/1994 | Cummings, Jr. ................ 705/2 |
| 5,519,607 A | | 5/1996 | Tawil |
| 5,649,117 A | * | 7/1997 | Landry ........................ 705/40 |
| 5,748,907 A | * | 5/1998 | Crane ............................ 705/2 |
| 5,805,676 A | * | 9/1998 | Martino .................... 379/93.17 |

FOREIGN PATENT DOCUMENTS

| GB | 2315350 | * | 1/1998 |
|---|---|---|---|

OTHER PUBLICATIONS

Kavanagh, K. T., Smith, T. R., Golden, G. S., Tate, N. P. and Hinkle, W. G., "Promotion of Patient Appointment Compliance in Indigent Pediatric Medical Care by Use of a Microcomputer," Annals of Otology, Rhinology & Laryngology, pp 755–760, Oct. 1989.*

Kavanagh, K. T., "The Delta Patient Management/Billing System", JAMA, vol. 263, pp 1717–1718, Mar. 23, 1990.*
Parrish, John M., Charlop, Marjorie H. and Fenton, Lisa R., "Use of a Stated Waiting List Contingency and Reward Opportunity to Increase Appointment Keeping in an Outpatient Pediatric Psychology Clinic", Journal of Pediatric Psychology, vol. 11, No. 1, p, Mar. 1986.*
"Utah Agents Spill Beans on Bank Ad", National Underwriter & Casualty, May 6, 1996.*
Dini, Eugene F., Linkins, Robert, W. and Chaney, Michael, "Effectiveness of Computer–Generated Telephone Messages in Increasing Clinic Visits", Archives of Pediatrics & Adolescent Medicine, vol. 149, pp 902–905, Aug. 1995.*
Gross, Alan M., Bishop, F. Walt, Reese, Dawn, Lollis, Teresa, Janke, Cindy, Hedden, Cindy and Smith, Steve, American Journal of Orthodontics and Dentofacial Orhopedics, vol. 93, No. 3, pp 259–260, Mar. 1988.*
Macharia, William M., Leon, Gladys, Rowe, Brian H., Stephenson, Barbara J. and Haynes, R. Brian, "An overview of Interventions to Improve Compliance With Appointment Keeping for Medical Services", JAMA, vol. 267, No. 13, pp 1813–1817, Apr. 1992.*

(List continued on next page.)

*Primary Examiner*—Joseph Thomas
*Assistant Examiner*—Christopher L. Gilligan
(74) *Attorney, Agent, or Firm*—Nexsen Pruet, LLC; Michael A. Mann

(57) ABSTRACT

A method and system for reinforcing regular chiropractic care comprising the establishment and maintenance of a policy of life insurance on a patient as long as the patient keeps each of a series of regularly scheduled, routine visits for chiropractic care. A programmed general purpose computer maintains the schedule, reminds the patient of upcoming appointments, compares the schedule to patient logs to verify that the schedule of appointments are being kept, and authorizes the policies of life insurance with a preselected insurance company, paying the premiums automatically by wire transfer.

26 Claims, 1 Drawing Sheet

OTHER PUBLICATIONS

Wesch, David, Lutzker, John R., Frisch, Larrry and Dillon, Michelle M., Journal of Behavior Medicine, vol. 10, No. 1, pp 91–101, Feb. 1987.*

Bigby, JudyAnn, Giblin, James, Pappius, Elizabeth M. and Goldman, Lee, JAMA, vol. 250, No. 13, pp 1742–1745, Oct. 1983.*

* cited by examiner

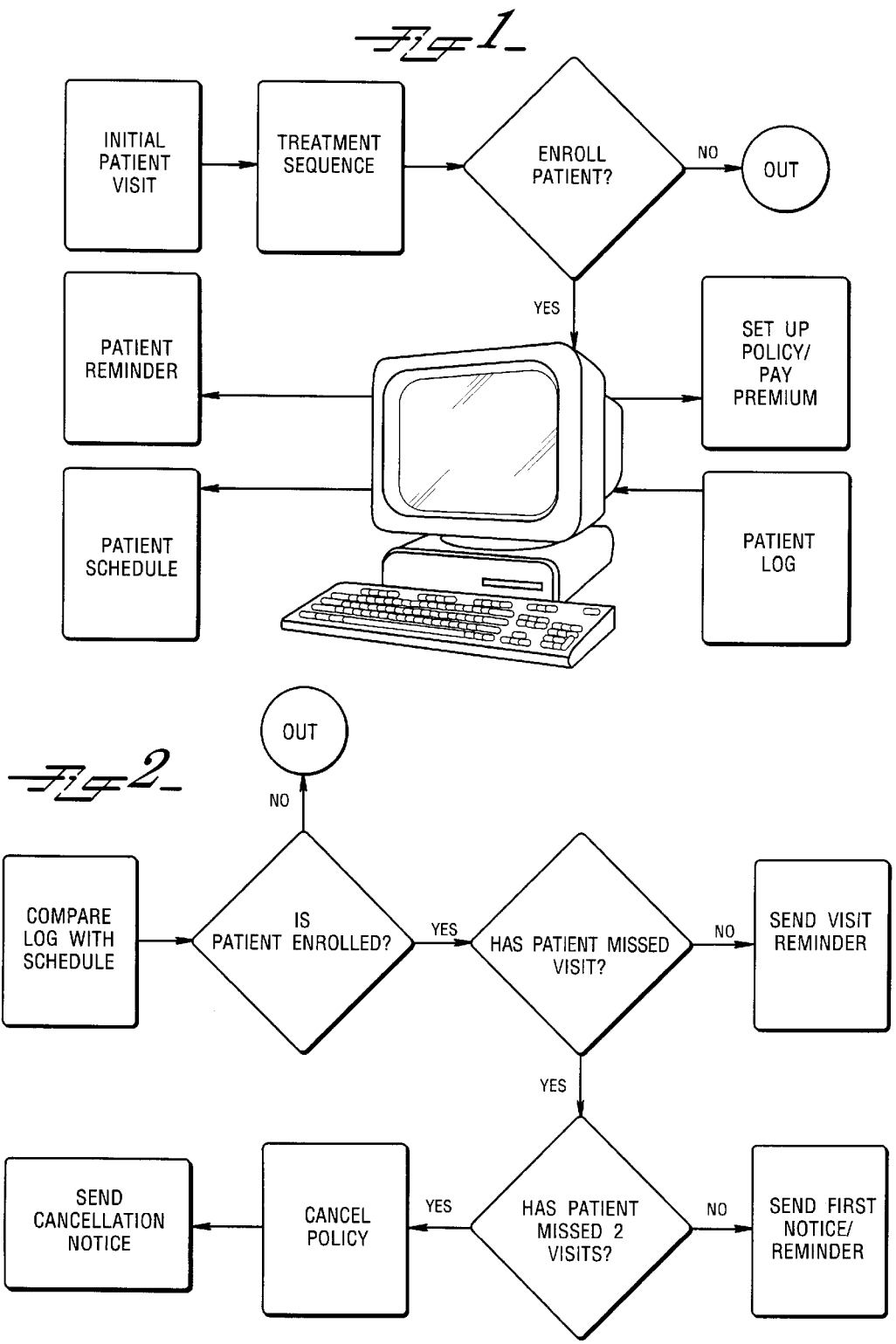

SYSTEM AND METHOD FOR REINFORCING REGULAR CHIROPRACTIC TREATMENT

The applicant claims the benefit of the date of filing a provisional patent application Ser. No. 60/055,239, filed Aug. 12, 1997.

BACKGROUND OF THE INVENTION

1. Field of the Invention

The present invention relates to the practice of chiropractic care. In particular, the present invention relates to coupling a basic life insurance policy to a system of regular chiropractic care.

2. Discussion of Background

Chiropractic health care is a well known and successfully used method of health restoration and enhancement. Chiropractors manage the biomechanical relationship of the spinal segments in relationship to each other as the central nervous system, peripheral nervous system, the protective meningeal barriers and all other tissues connected to the spine.

Individuals who suffer from spinal improprieties are cared for by chiropractors using various techniques to stabilize and correct their spinal columns, resulting in relief from spinal aberrations and the correction of the resultant disorder.

This is a wellness/maintenance program for the detection, correction and prevention of a spinal impropriety which can be called a vertebral subluxion complex. A vertebral subluxion complex is defined as a vertebra or vertebrae that has lost the normal positional relationship with the vertebra or vertebrae above and/or below to an extent less than a luxation resulting in any of the following improprieties.

1. Aberrant pressures within the intervertebral foramina altering the functional capacities of the following:
   A. Spinal nerve including impeding impulse movement and/or Axonal transport System;
   B. Dural sleeve and its relationship with the meninges as it affects the central spinal fluid flow;
   C. Sinu Vertebral Nerve (recurrent nerve fiber);
   D. Spinal artery;
   E. Spinal veins;
   F. Lymphatic vessels; and
   G. Other Soft tissues (e.g., adipose tissue areolar connective tissue)

2. Abnormal positioning of the spinal articular facets sufficient to:
   A. Inappropriately stimulate the propioceptive nervous system, which is responsible for the spinal stability and equilibrium;
   B. Contorsional stress upon the interforaminal ligaments;
   C. Arouse irritative factors to the facet surfaces which will lead to eroding or destructive forces to the hyaline lining of the joint surface;
   D. A compromising of the joint capsule and ligamental flavum stretching, tearing, weakening, hardening and buckling;
   E. Contorting of the synovial tissues resulting in reduced synovial fluids (slower synovial fluid exchange); and
   F. Creates contentions responses to adjacent soft tissues and bony structures resulting in edema, bony remodeling and tissue thickening and buckling.

3. Wrenching of the intervertebral disc resulting in imperilment of tissues which help comprise the functional disc, namely the annulus, nucleus pulposa, posterior longitudinal ligament and fibers of sharpie resulting in a loss of the viscoelastic and elastic properties.

4. Divisive compression forces against the vertebral body compromising the integrity of the cartilaginous endplates, cortex and canecellous bone.

5. Muscle Tonicity change—"Irritation at any spinal segment, but the cervical ones in particular, may result in hypertonous of these long muscles and traction of the collagenous attachments to the occipital cranium . . . In this way thoracic and even lumbosacral lesions such as postural malalignments and arthrosis or myofascitis from local or remote (visceral) causes, have been shown to produce cephalalgia and its concomitants." according to Gregory P. Grieve, FLSP, DIPTP, in Common Vertebral Joint Problems (1988).

6. Failure of the ligaments and bone to correctly interface.

Individuals who knowingly or unknowingly suffer from subluxations and are treated by chiropractors using various techniques to correct spinal subluxations, with the result being immeasurably physiologically constructive along with the alleviation of pain.

What is also known but not generally appreciated is that individuals who regularly visit a chiropractor for care live longer than those who do not. Studies have shown that routine, regular visits to a chiropractor result in a statistically significant increase in longevity.

Many of those who seek the help of chiropractors for the relief of subluxation have modest incomes and therefore find it difficult to meet all of their financial needs. One of those needs is for life insurance. Life insurance, at a basic level, is very important to people. Many who have ample incomes carry excess life insurance for a variety of reasons involving estate planning, but, for those with modest incomes, life insurance is used for paying for the cost of a funeral and burial expenses. For those of limited income, life insurance spares their surviving spouse and children the necessity of having to pay these unexpected costs.

For many people, then, the cost of life insurance competes with the cost of getting treatment for aches and pains. There exists a need for reconciling these competing costs.

SUMMARY OF THE INVENTION

According to its major aspects and broadly stated, the present invention is a system and method for reinforcing chiropractic care; that is, for encouraging those who wish to benefit from regular, routine chiropractic care by providing them with a life insurance policy that remains in effect as long as they keep their regularly scheduled appointments, and without additional cost to the patient.

Furthermore, by undergoing regularly scheduled maintenance chiropractic care, they live longer and the life insurance can essentially pay for itself.

To implement this system, patient data is recorded into a programmable general purpose computer, which data has been obtained from an initial patient visit. The data is used by the computer to schedule the regular appointments for treatment and to authorize the issuance of policies of life insurance for the participating individuals. The computer also arranges to pay premiums for the insurance on a batchwise basis by wire transfer. If a patient misses appointments, the policy is canceled and notice is sent to the patient.

The combination of routine chiropractic care and life insurance policies is a major feature of the present invention. Because those undergoing routine, regular chiropractic care live longer, the cost of their life insurance is lower because (1) the insurance premiums can be invested longer, and (2) the patients are screened for the general state of their health before being enrolled into this program, which is not usually the case for basic, low-face-value life insurance. Furthermore, having basic life insurance and regular chiropractic treatment reinforce each other, so that many individuals will be determined to keep their regularly scheduled visits for routine chiropractic treatment because of the free life insurance policy, and thereby benefit by the correspondingly greater longevity.

Another feature of the present invention is the use of a computer to authorize the life insurance policies, pay premiums and maintain patients' treatment schedules. By using a computer for these tasks, the process is simplified and streamlined. The computer can also be used to send health longevity bulletins on a monthly basis.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings, FIG. 1 is a flow chart of a system for reinforcing chiropractic care according to a preferred embodiment of the present invention; and FIG. 2 is a flow chart of a detail of the system for reinforcing chiropractic care according to a preferred embodiment of the present invention.

DETAILED DESCRIPTION OF A PREFERRED EMBODIMENT

Referring now to FIGS. 1 and 2, there are illustrated flow charts of the system for reinforcing regular chiropractic care by having the chiropractor pay the premiums on a policy of life insurance as an incentive to encourage patients to visit the chiropractor on a regular, routine basis for health maintenance. Moreover, by undergoing that regimen of treatment, statistically, the patient's longevity would be expected to increase over what it would be without the treatment, thus making the insurance more affordable.

When a patient visits a chiropractor for an initial visit, presumably for care for care of health related problems, which could be aches, pains or dysfunction, he undergoes a preliminary examination, which includes the obtaining of basic information and an examination which may include x-rays. The doctor will issue a report of findings that explains the problem to the patient and prescribes a protocol of spinal care for the correction of the cause of the aches, pains, discomfort or disease. At the conclusion of the treatment plan, if the patient has responded appropriately (correction of the spinal subluxation complex) which coincides with a pattern of good spinal health, the patient will be asked to enroll in the present program. If the patient declines, no further action is necessary. If the patient is not in reasonably good health, no offer to participate will be extended.

If the patient wishes to enroll, a computer application takes over the maintenance of the present system. This application, which programs a general purpose computer, reads the patient file history to input patient data into a data base in the computer's memory, and sets up the appointment schedule, which is also input to the data base. The schedule is preferably monthly but need only be at regular intervals and relatively frequent. If a next appointment would fall on a weekend or holiday (or a day when it cannot be scheduled for some other reason), then it is rescheduled by the computer for the nearest business day where time is available. A notice of the appointment as scheduled is sent to the patient. This notice may be in the form of a letter or a computer controlled telephone call to the patient's home telephone number with a prerecorded message. If the latter, the message may simply be a prerecorded announcement of the date and time of the visit, or it may include a rescheduling capability using either the pushbuttons of the patient's telephone or voice recognition technology to record responses from the patient. In either case, the computer controller will case the patient to be reminded of the upcoming appointment. The computer, as programmed, will also generate a patient schedule for the doctor's office that includes the appointments of all enrolled and non-enrolled patients.

The computer will authorize the policies of insurance by printing out a letter or by faxing a letter or a list of all patients being enrolled to a participating life insurance company along with information confirming a wire transfer of the premium for the policy. The list will include administrative information such as the name, address, telephone number, date of birth, gender, occupation, marital status, etc. of the proposed insured, along with the name and address of the insured's beneficiary. Ideally, on a periodic and batchwise basis, preferably weekly or biweekly, the computer will contact the insurance company and transmit by facsimile a listing of all new enrollees, all patients to be removed from participation, and all premiums being transferred to the insurance company's designated account.

The computer controller will effect an electronic fund transfer from an account maintained by the chiropractor to one designated by the insurance company. Monthly premiums (or less often if convenient) will be transferred from the chiropractor's account to the insurance company's account for each patient who has kept the monthly appointment.

Periodically, preferably daily, the patient log maintained by the doctor of all patients visiting his or her office will be input to the computer. The log information, as illustrated in FIG. 2, will be compared to the schedule to determine if those patients who are enrolled have kept their most recent appointments. If they did not, but only one appointment has been missed, then a notice letter is prepared automatically for sending to the patient as a reminder that, if appointments are not kept, the policy of insurance will be canceled. In addition, the patient's data will be updated to indicate that an appointment has not been kept.

If the patient has missed two consecutive appointments, then a notice of policy cancellation is prepared for sending and the insurance company is immediately notified to cancel the policy.

If the patient has kept an appointment, a reminder of a next scheduled visit is sent to the patient in advance of the upcoming appointment. Appointments will preferably be scheduled every thirty days. From the first visit under the program each year, the annual premium for the term life insurance policy will be paid. If the patient expires while enrolled, the face value of the policy will be paid to the patient's designated beneficiary.

In use in its preferred embodiment, as soon as the patient assents to become enrolled in the system, nearly every step may be done automatically. "Automatically" means that, by suitable software and perhaps with additional and well-known hardware, such as printers and modems, the step can be left to the computer controller and needs no human intervention. The computer controller will access patient data and load it into a data base. The computer will then generate a monthly (or at least a regular) schedule of appointments for the patient.

In advance of each appointment, the computer will automatically generate a reminder for the patient, preferably by software and modem connection to a telecommunication system so that the computer controller can telephone the patient and, using a conventional audible messaging system, remind the patient of the upcoming appointment and obtain the patient's confirmation that the appointment will be kept. One type of messaging system currently in use dials the patient and assembles a series of pre-recorded words to effect a complete message reminding the patient (who is named) of the date and time of the meeting and then prompts the patient to confirm or reschedule the appointment by pressing various buttons on the patient's telephone. If the patient cannot keep the appointment, the appointment can be rescheduled either telephonically or by having the patient call the office. Alternatively, the computer controller can generate a note or letter reminding the patient and requesting that the patient call if the time and date of the appointment is inconvenient. Appointment reminder and scheduling software is will known and in use.

The chiropractor's staff loads patient logs into a computer frequently, i.e., daily, which can be accessed by the computer controller to enter the log information into the data base along with the patient schedule. By having the controller compare the appointment schedule with the log data, missed appointments can be determined. As long as appointments are kept, the chiropractor will continue to make the premium payments to the insurance company insuring the life of the patient.

Those premiums can be paid by electronic fund transfer authorized by the computer controller provided that the appointments have been kept. The transfers are effected between an account designated by the chiropractor and the account designated by the insurance company.

In the event a patient fails to keep an appointment, preferably in the event two appointments are missed, the computer controller can cancel the policy of insurance, delete the scheduled premium payments, and notify the patient that insurance coverage has been canceled for failing to keep appointments.

It will be clear to those familiar with the importance of life insurance to a segment of the population that there are other circumstances where the same approach can be employed. For example, if an individual is obese and is participating in a program of moderate diet and exercise, that individual can also be encouraged by providing a policy of insurance as long as the individual continues to participate in the program. Other examples will also be apparent to those who are seeking ways to encourage activities and behavioral patterns that contribute in some way to overall longevity.

It will be apparent to those skilled in the art that many changes and substitutions can be made to the preferred embodiment herein described without departing from the spirit and scope of the present invention, as defined by the appended claims.

What is claimed is:

1. A method for reinforcing regular chiropractic care with respect to a patient, said method comprising the steps of:
   entering data regarding a patient into a memory of a computer;
   setting up a series of appointments for said patient for chiropractic care, said series of appointments being recorded in a database maintained in said memory of said computer;
   authorizing the issuance of a policy of life insurance on the life of said patient from an insurance company;
   automatically reminding said patient of each appointment in advance of said each appointment in said series of appointments;
   verifying said patient has kept said each appointment; and
   automatically making premium payments for said policy of life insurance on said patent to said life insurance company so long as said patient keeps said each appointment.

2. The method as recited in claim 1, further comprising the step of entering patient log data into said database of said memory of said computer.

3. The method as recited in claim 1, further comprising the step of entering patient log data into said database of said memory of said computer and wherein said verifying step further comprises comparing said entered patient log data with said series of appointments to determine if said patient has kept said appointments.

4. The method as recited in claim 1, further comprising the step of entering patient log data into said database of said memory of said computer, wherein said verifying step further comprises comparing said entered patient log data with said series of appointments to determine if said patient has kept said appointments, and further comprising the step of cancelling said policy of insurance if said patient has not kept said appointments.

5. The method as recited in claim 1, wherein said automatically reminding step further comprises the step of making a computer-controlled telephone call to said patient.

6. The method as recited in claim 1, wherein said automatic reminding step further comprises the step of generating via said computer an appointment reminder letter for mailing to said client.

7. The method as recited in claim 1, wherein said automatically making premium payments step further comprises the step of making via said computer an electronic fund transfer from a preselected account to an account designated by said insurance company.

8. The method as recited in claim 1, wherein said automatically making premium payments step further comprises the steps of:
   printing a check via a printer controlled by said computer drawn on an account to pay said premiums; and
   mailing said check to said insurance company.

9. The method as recited in claim 1, further comprising the steps of:
   examining said patient; and
   conducting a protocol of spinal care prior to entering said patient data into said memory of said computer.

10. The method as recited in claim 1, further comprising the step of cancelling said policy of insurance if said patient misses appointments.

11. A method for reinforcing regular chiropractic care with respect to a patient, said method comprising the steps of:
   examining a patient;
   entering data regarding said patient into a memory of a computer;
   setting up a series of appointments for said patient for chiropractic care, said series of appointments being recorded in a database maintained in said memory of said computer;

authorizing the issuance of a policy of life insurance on the life of said patient from an insurance company;

automatically reminding said patient of each appointment in advance of said each appointment in said series of appointments;

verifying said patient has kept said each appointment;

automatically making premium payments for said policy of life insurance on said patent to said life insurance company so long as said patient keeps said each appointment; and entering patient log data into said database of said memory of said computer.

12. The method as recited in claim 11, wherein said verifying step further comprises comparing said entered patient log data with said series of appointments to determine if said patient has kept said appointments.

13. The method as recited in claim 11, wherein said verifying step further comprises comparing said entered patient log data with said series of appointments to determine if said patient has kept said appointments, and further comprising the step of cancelling said policy of insurance if said patient has not kept said appointments.

14. The method as recited in claim 11, wherein said automatically reminding step further comprises the step of making a computer-controlled telephone call to said patient.

15. The method as recited in claim 11, wherein said automatic reminding step further comprises the step of generating via said computer an appointment reminder letter for mailing to said client.

16. The method as recited in claim 11, wherein said automatically making premium payments step further comprises the step of making via said computer an electronic fund transfer from a preselected account to an account designated by said insurance company.

17. The method as recited in claim 11, wherein said automatically making premium payments step further comprises the steps of:

printing a check via a printer controlled by said computer drawn on an account to pay said premiums; and mailing said check to said insurance company.

18. The method as recited in claim 11, further comprising the step of conducting a protocol of spinal care prior to entering said patient data into said memory of said computer.

19. The method as recited in claim 11, further comprising the step of cancelling said policy of insurance if said patient misses appointments.

20. A method for reinforcing regular chiropractic care with respect to a patient, said method comprising the steps of:

examining a patient;

conducting a protocol of spinal care prior to entering patient data into said memory of said computer, entering data regarding said patient into a memory of a computer;

setting up a series of appointments for said patient for chiropractic care, said series of appointments being recorded in a database maintained in said memory of said computer;

authorizing the issuance of a policy of life insurance on the life of said patient from an insurance company;

automatically reminding said patient of each appointment in advance of said each appointment in said series of appointments;

verifying said patient has kept said each appointment;

automatically making premium payments for said policy of life insurance on said patent to said life insurance company so long as said patient keeps said each appointment; and cancelling said policy of insurance if said patient misses appointments.

21. The method as recited in claim 20, further comprising the step of entering patient log data into said database of said memory of said computer.

22. The method as recited in claim 20, further comprising the step of entering patient log data into said database of said memory of said computer and wherein said verifying step further comprises comparing said entered patient log data with said series of appointments to determine if said patient has kept said appointments.

23. The method as recited in claim 20, wherein said automatically reminding step further comprises the step of making a computer-controlled telephone call to said patient.

24. The method as recited in claim 20, wherein said automatic reminding step further comprises the step of generating via said computer an appointment reminder letter for mailing to said client.

25. The method as recited in claim 20, wherein said automatically making premium payments step further comprises the step of making via said computer an electronic fund transfer from a preselected account to an account designated by said insurance company.

26. The method as recited in claim 20, wherein said automatically making premium payments step further comprises the steps of:

printing a check via a printer controlled by said computer drawn on an account to pay said premiums; and mailing said check to said insurance company.

* * * * *